(12) United States Patent
Leese et al.

(10) Patent No.: US 6,495,707 B1
(45) Date of Patent: Dec. 17, 2002

(54) PROCESS AND APPARATUS FOR PRODUCTION OF ORGANOMETALLIC COMPOUNDS

(75) Inventors: Albert Barry Leese, Alsager (GB); Graham Williams, Wirral (GB); Lesley Margaret Smith, Wirral (GB); Simon Andrew Rushworth, Wirral (GB); Phillip Reeve Jacobs, Chester (GB); Elizabeth Ann McKinnell, Wirral (GB); David Joseph Houlton, Wigan (GB)

(73) Assignee: Epichem Limited, Wirral Merseyside (GB)

( * ) Notice: Subject to any disclaimer, the term of this patent is extended or adjusted under 35 U.S.C. 154(b) by 0 days.

(21) Appl. No.: 09/868,377

(22) PCT Filed: Sep. 9, 1999

(86) PCT No.: PCT/GB99/03007
§ 371 (c)(1),
(2), (4) Date: Jun. 18, 2001

(87) PCT Pub. No.: WO00/37475
PCT Pub. Date: Jun. 29, 2000

(30) Foreign Application Priority Data

Dec. 19, 1998 (GB) ............................................. 9827957

(51) Int. Cl.⁷ ............................. C07F 5/00; B01J 14/00
(52) U.S. Cl. ........................... 556/1; 556/187; 422/129; 422/145; 422/146
(58) Field of Search ................... 556/1, 187; 422/129, 422/145, 146

(56) References Cited

U.S. PATENT DOCUMENTS

| | | | |
|---|---|---|---|
| 3,480,654 A | * 11/1969 | Sundermeyer et al. | ......... 556/1 |
| 4,118,409 A | 10/1978 | Eidt et al. | ............... 260/448 A |
| 5,372,790 A | * 12/1994 | Shirtum et al. | ............. 422/135 |
| 5,473,090 A | * 12/1995 | Smit et al. | ..................... 556/1 |
| 5,543,537 A | 8/1996 | Eisenberg et al. | .......... 556/157 |
| 5,756,786 A | * 5/1998 | Power et al. | ................... 556/1 |
| 5,817,847 A | 10/1998 | Giolando | ....................... 556/1 |

FOREIGN PATENT DOCUMENTS

| | | |
|---|---|---|
| DE | 1158997 | 12/1963 |
| EP | 0130005 A2 | 1/1985 |
| EP | 0218994 A2 | 4/1987 |
| EP | 0272560 A2 | 6/1988 |
| GB | 2123423 A | 2/1984 |
| GB | 2304104 A | 3/1997 |

OTHER PUBLICATIONS

Fukin et al., Zhurnal Obshchef Khimii, vol. 47, No. 11, *Model Description of Reaction Leading to the Synthesis of Trimethylgallium*, XP–002121775, pp. 2410–2415, Nov. 1977.
WPI Abstract No. 73–76879U/197350 and SU 375293A, *Trimethyl–gallium and indium prepn—from gallium or indium trihalide with trimethylaluminium/potassium chloride complex*, Heteroorganic Compds Inst. date unknown.
WPI Abstract No. 72–43149T/197227 and NL 135591B, *Trialkylgallium cpds—by reacting gallium salts with trailkylalumini*, Siemens–Schuckertwerke AG, date unknown.
Gaines et al., Chemical Abstracts, vol. 81, No. 23, Abstract No. 152311, *Trimethylgallium*, XP002121776, Dec. 1974.
Fukin et al., Chemical Abstracts, vol. 81, No. 17, Abstract No. 105607, *Alkylation of gallium chloride by trimethylaluminum*, XP002121777, Dec. 1974.

* cited by examiner

Primary Examiner—Porfirio Nazario-Gonzalez
(74) Attorney, Agent, or Firm—Thompson Coburn LLP

(57) ABSTRACT

A process and apparatus for the continuous production of organometallic compounds from a metal precursor and an alkylating agent. The reactants are delivered separately to a reaction centre (26) in a distillation column (2) wherein the reaction is maintained at a predetermined temperature to allow collection of the vaporised organometallic compound from the top of the column and removal of the waste products from the bottom of the column.

31 Claims, 1 Drawing Sheet

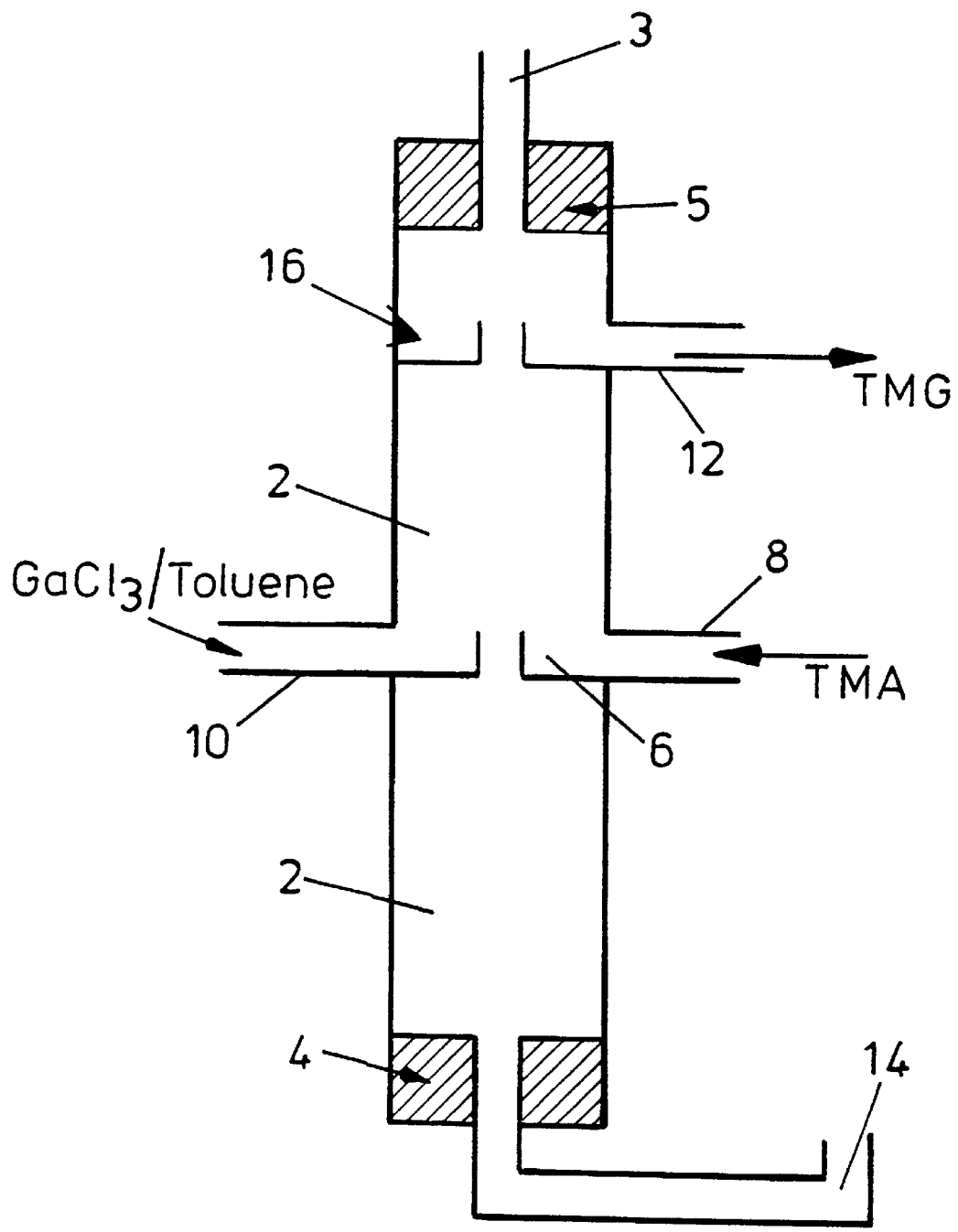

PROCESS AND APPARATUS FOR PRODUCTION OF ORGANOMETALLIC COMPOUNDS

The present invention relates to an improved process and apparatus for the production of organometallic compounds, in particular organo compounds of Group 3a metals, especially trimethylgallium.

Organometallic compounds such as trimethylgallium are commonly employed as a gallium source in the fields of epitaxial semi-conductor growth and/or processing, vapour or plasma etching, plasma deposition or thin film deposition, for example metalorganic chemical vapour deposition (MOCVD). The compounds are generally prepared using a batch process wherein the reactants are fed into a reaction vessel and the product is collected once the reaction is complete. Trimethylgallium is normally prepared by means of such a batch process using gallium trichloride and a suitable alkylating agent such as a Grignard reagent, Lithium reagent or trialkylaluminium. This process provides compounds that are sufficiently pure but requires the use of large reaction vessels to produce a sufficient yield of product. The production rate of the compound is also limited due to the necessity to charge the reaction vessel, add specified amounts of the reactants, allow the reaction to take place and then collect the product and clean the vessel before commencing the process again. Cleaning the equipment between runs of the reaction may also lead to increased contamination of the product.

GB-A-2 123 423 (The Secretary of State for Defence) relates to the preparation of trialkylgallium compounds using a dialkylether. However, such a reagent can result in the product containing oxygen impurities. DE 11 58 977 (Siemens-Sciuckertwerke AG) also describes a process for the preparation of trialkylgallium compounds, whereby one equivalent of gallium trichloride is added to three equivalents of an aluminium trialkyl in solution in a hydrocarbon solvent or an ether. The process is carried out as a batch process to enable sufficiently pure product to be obtained. Similarly, Inorg. Synth (1974) 15, 203-7 and Chemical Abstracts, vol. 81, no. 17, 28 October 1974 (1974-10-28) & TR. Khim, Khim. Tekhnol (1973), (4), 40-41 relate to the preparation of trialkyl metal compounds using batch processes.

It is an aim of the present invention to provide an improved process and apparatus for the preparation of organometallic compounds, in particular the production of trimethylgallium, which overcomes the above mentioned drawbacks.

Accordingly, a first aspect of the present invention provides a continuous process for the preparation of an organometallic compound comprising the steps of delivering a metal precursor and an alkylating agent separately to a reaction centre, allowing the precursor to react with the alkylating agent, maintaining the reaction centre at a predetermined temperature to cause vapourisation of the organometallic compound and collecting the organometallic compound.

A second aspect of the present invention provides an apparatus for the preparation of an organometallic compound, the apparatus comprising at least two delivery conduits and a distillation column having a reaction centre and an outlet wherein each conduit transports a metal precursor and an alkylating agent respectively to the reaction centre to allow the reactants to react together, the temperature of the apparatus being maintained such as to allow collection of the vapourised organometallic compound from the outlet thereby enabling continuous production of the organometallic compound.

The process of the present invention may be used to prepare any organometallic compound wherein the product is a volatile liquid and the by-products are less volatile.

The continuous process for the preparation of organometallic compounds requires the reactants to be fed separately into a reaction section which is preferably provided in the centre of the distillation column. Preferably the outlet is provided at or near the top of the column for collection of the product and a further outlet is provided at or near the base of the column for removal of any waste products. The equipment is maintained at specified temperatures to control the rate of removal of the product from the top of the reaction column, with the non-vapourised waste products being removed from the base of the column. The continuous delivery of the reactants in specified amounts and at a predetermined rate into the reaction section, together with the maintenance of a specified temperature/pressure differential in the column enables a continuous production of the organometallic compound to be achieved. The rate of addition of the reactants may be controlled by means of appropriate flow controllers.

The rate of removal of the product from the top of the column should be carefully controlled to avoid a build up of the product in the column and a consequence loss of the product from the base of the column with the waste. Suitable conventional instrumentation systems such as a flow controller and temperature/pressure differential, may be used to maintain the required rate of removal of the product.

The continuous process relies on an equilibrium being set up in the column such that the product goes up the column and the waste products move down for their removal at the base, for example by means of a simple overflow leg. A number of factors effect the maintenance of the equilibrium, such as the temperature of the column, the addition rates of the reactants and the take off rate of the product. The conditions employed will vary according to the reactants and the organometallic compound being produced. The temperature is preferably fixed and the main control for a set of addition rates will then be the take off rate of the product.

Preferably, the distillation column for use in the present invention is fitted with a boiler at the base and a condenser at the top, the design of which will be dependent on the heat of the reaction to be carried out in the column. Importantly, means should be provided to allow the control of the reflux ratio applied to the top of the column and to remove the heat produced during the reaction from the reaction zone.

Any suitable distillation column may be used for carrying out the process of the present invention such as packed or plate distillation columns. The column should be equipped with sufficient plates in a stripping section to ensure removal of all the product from the stream leaving the base of the column and sufficient plates in the rectifying section to ensure the pure product leaves the top of the column.

Preferably, the metal precursor is added in a suitable solvent, such as toluene. It is preferable to prime the reaction centre with the solvent prior to commencing the reaction. Preferably, the solvent has a lower volatility than the organometallic compound to allow the pure product to be collected from the top of the column while the solvent leaves the base of the column with the by-products.

The reaction centre is preferably heated prior to commencing delivery of the reactants to the reaction centre in order to achieve a steady reflux. Preferably alkylating agent is added to the reaction centre prior to the metal precursor to ensure there is an excess amount of agent present.

Collection of the product is preferably commenced once a constant temperature corresponding to the boiling point of the product is recorded near to the top of the column, preferably around 2–5 cm from the top of the column. Preferably, collection of the product is halted if a rise in temperature is recorded and re-commended once the temperature drops back to the boiling point of the product.

The process of the present invention is particularly suitable for the preparation of Trimethylgallium in a continuous fashion by the reaction between trimethylaluminium (TMA) and gallium trichloride in a suitable solvent. The reaction is extremely exothermic and virtually instantaneous and it is desirable to move heat as quickly as possible from the reaction zone in order to prevent unwanted side reactions.

The reaction centre is preferably heated to a temperature between 120° C. to 140° C, more preferably 130° C. until a steady reflux is achieved. The reactants may then be added, preferably commencing with the TMA. The ratio of active ingredients in the column should be such that there is an excess of TMA at all times to ensure full conversion of the gallium trichloride to trimethylgallium. A ratio of 5:1 TMA to gallium trichloride is preferred but other ratios may be used, such as 4:1 or 3.5:1.

The TMA and $GaCl_3$ may be added at any predetermined rate depending upon the production rate of product required. For example, the TMA and $GaCl_3$ may be added at a rate of 90 g/hr and 75 g/hr respectively to give a production rate of 30 g/hr. Alternatively, addition rates of 250 g/hr and 315 g/hr may be used to provide a production rate of 115 g/hr.

Collection of the trimethylgallium is commenced once a steady temperature of 56° C. is maintained near the top of the column.

The solvent is preferably one which is less volatile than the trimethylgallium, such as toluene to ensure that pure product is collected as a vapour.

The present invention will now be further illustrated by means of the following Examples which describe the continuous preparation of trimethylgallium using the process and apparatus of the present invention and with reference to the accompanying drawing which is a schematic diagram of one embodiment of the apparatus of the present invention.

EXAMPLE 1

The main reaction column 2 was packed and provided with an inert atmosphere through inlet 3. The column was initially primed with the solvent, anhydrous Toluene (200 mls). The boiler 4 at the bottom of the column was heated to 130° C. to establish a steady reflux in the column by means of the condensor 5. Trimethylaluminium (TMA) was then added through an inlet pipe 8 to the centre 6 of the reaction column approximately two minutes before the metering of gallium trichloride ($GaCl_3$) in toluene solution into the column was commenced through a separate inlet 10. This ensured that excess alkylating agent was present to minimize the potential for incomplete product formation.

The addition rates of the TMA and $GaCl_3$ were set at 90 g/hr and 75 g/hr respectively (5:1 molar ratio of active components) using the appropriate flow controllers. This leads to a theoretical trimethylgallium (TMG) production rate of 30 g/hr. The temperature at the collection point (16) of the product gradually decreased as sufficient TMG was formed to displace the toluene as the most volatile component. Once a steady reading of 56° C. was achieved collection of the product from the upper outlet pipe 12 was commenced with the rate of collection being controlled such as to maintain a constant temperature of 56° C. in the column approximately 1–2 inches below the take off point. Any temperature increase indicating a presence of toluene resulted in a halt in collection until a constant temperature of 56° C. was again maintained. The waste products, (i.e. $Me_2$AlCl, TMA and toluene with trace partially alkylated gallium species) were forced down the boiler and removed by an overflow pipe 14 into a dilution vessel (not shown).

The apparatus was run for a total of 7 hours during which time 140 g of TMG were isolated (68% yield).

EXAMPLE 2

The process described in Example 1 above was repeated but employing addition rates for the reactants TMA and $GaCl_3$ in toluene of 90 g/hr and 100 g/hr respectively (4:1 molar ratio of active components leading to a theoretical TMG production rate of 40 g/hr.

The apparatus was run for a total of 10 hours during which time 198 g of TMG were isolated. (50% yield).

EXAMPLE 3

The process described in Example 1 above was repeated but employing addition rates for the reactants TMA and $GaCl_3$ in toluene of 250 g/hr and 315 g/hr respectively (3.5:1 molar ratio of active components) leading to a theoretical TMG production rate of 115 g/hr.

The equipment was run for a total of 3.5 hours during which time 220 g of TMG were isolated. (55% yield).

The process and apparatus of the present invention allow the continuous production of an organometallic compound with sufficient yields of product. This enables the ready scale up of the process without the need for huge plant vessels and additional processing steps. For example, a batch process may use a 200L reaction vessel that takes 12–13 hours per batch. The continuous process allows the use of much smaller vessels, for example, 10L holding vessels, to produce a satisfactory rate of production. Additionally, the process avoids the need for frequent dismantling and cleaning of the reaction vessel thereby reducing contamination of the product, increasing production rates and improving safety ratings.

What is claimed is:

1. A continuous process for the preparation of an organometallic compound comprising the steps of delivering a metal precursor and an alkylating agent separately to a reaction centre wherein the precursor reacts with the alkylating agent to form the organometallic compound, maintaining the reaction centre at a predetermined temperature to cause vapourisation of the organometallic compound and collecting the organometallic compound.

2. A continuous process as claimed in claim 1 wherein the product is a volatile liquid and by-products of the reaction are less volatile.

3. A continuous process as claimed in claim 1, wherein the reactants are fed separately into the reaction center which is provided in the center of the distillation column.

4. A continuous process as claimed in claim 3, wherein the product is collected from the top of the column and the by-products are removed from the base of the column.

5. A continuous process as claimed in claim 4, wherein the process is maintained at specified temperatures to control the rate of removal of the product from the top of the column, with the non-vapourised by-products being removed from the base of the column.

6. A continuous process as claimed in claim 5 wherein continuous delivery of reactants in specified amounts and at a predetermined rate into the reaction section, together with the maintenance of a specified temperature/pressure differential in the column enables the continuous production of the organometallic compound to be achieved.

7. A continuous process as claimed in claim 6 wherein the rate of addition of the reactants is controlled by means of flow controllers.

8. A continuous process as claimed in claim 5, wherein the rate of removal of the product is controlled to prevent build up of the product in the column.

9. A continuous process as claimed in claim 6, wherein the temperature is fixed and the main control for a set of addition rates is the removal rate of the product.

10. A continuous process as claimed in claim 9 wherein the reflux ratio applied to the top of the column is controlled.

11. A continuous process as claimed in claim 1, wherein heat produced during the reaction is removed from the reaction zone.

12. A continuous process as claimed in claim 1 wherein the metal precursor is added in a suitable solvent.

13. A continuous process as claimed in claim 12 wherein the reaction centre is primed with the solvent prior to commencement of the reaction.

14. A continuous process as claimed in claim 12, wherein the solvent has a lower volatility than the organometallic compound to allow pure product to be collected separately from the solvent.

15. A continuous process as claimed in claim 1 wherein the reaction center is heated prior to commencing addition of the reactants in order to achieve a steady reflux.

16. A continuous process as claimed in claim 1, wherein alkylating agent is added to the reaction center prior to the metal precursor to ensure excess against is present.

17. A continuous process as claimed in claim 1, wherein collection of the product is commenced once a constant temperature corresponding to the boiling point of the product is recordal near to the top of the column.

18. A continuous process as claimed in claim 1 for the preparation of trimethylgallium by the reaction between trimethyaluminium and gallium trichloride in a suitable solvent.

19. A continuous process as claimed in claim 18, wherein the reaction centre is heated to 120° C. to 140° C. to achieve a steady reflux before commencement of the reactants.

20. A continuous process as claimed in claim 19, wherein the reaction centre is heated to 130° C. until a steady reflux is achieved.

21. A continuous process as claimed in claim 18, wherein the addition of trimethylaluminium to the reaction center is commenced prior to the addition of gallium trichloride.

22. A continuous process as claimed in claim 18, wherein the ratio of trimethylaluminium to gallium trichloride in the column is 5:1.

23. A continuous process as claimed in claim 18, wherein trimethylaluminium and gallium trichloride are added at a rate of 90 g/hr and 75 g/hr respectively to give a production rate of 30 g/hr.

24. A continuous process as claimed in claim 18, wherein trimethylaluminium and gallium trichloride are added at a rate of 250 g/hr and 315 g/hr respectively to give a production rate of 115 g/hr.

25. A continuous process as claimed in claim 18, wherein collection of trimethylgallium is commenced once a steady temperature of 56° C. is obtained at the top of the column.

26. A continuous process as claimed in claim 18, wherein the solvent is toluene.

27. An apparatus for the preparation of an organometallic compound, the apparatus comprising at least two delivery conduits and a distillation column having a reaction centre and an outlet, wherein each conduit transports a metal precursor and an alkylating agent respectively to the reaction centre to allow the reactants to react together to form the organometallic compound, the temperature of the apparatus being maintained such as to allow collection of the vapourised organometallic compound from the outlet thereby enabling continuous production of the organometallic compound.

28. An apparatus as claimed in claim 27, wherein the outlet is provided at or near the top of the column for collection of the product and a further outlet is provided at or near the base of the column for removal of by-products.

29. An apparatus as claimed in 27, wherein the distillation column is provided with a boiler at the base of thereof and a condenser at the top.

30. An apparatus as claimed in claim 27, wherein means is provided to control the reflux ratio applied to the top of the column.

31. An apparatus as claimed in claim 27, wherein means is provided for removal of the heat produced during the reaction from the reaction zone.

* * * * *